（12）United States Patent
Shi et al.

(10) Patent No.: US 11,950,958 B2
(45) Date of Patent: *Apr. 9, 2024

(54) ADAPTIVE PULSING FOR SONOTHROMBOLYSIS TREATMENT

(71) Applicant: KONINKLIJKE PHILIPS N.V., Eindhoven (NL)

(72) Inventors: William Tao Shi, Wakefield, MA (US); Jonathon Thomas Sutton, Boston, MA (US); Jeffry Earl Powers, Bainbridge Island, WA (US); Ralf Seip, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 129 days.

This patent is subject to a terminal disclaimer.

(21) Appl. No.: 17/576,389

(22) Filed: Jan. 14, 2022

(65) Prior Publication Data

US 2022/0133277 A1 May 5, 2022

Related U.S. Application Data

(63) Continuation of application No. 16/469,764, filed as application No. PCT/IB2017/057825 on Dec. 12, 2017, now Pat. No. 11,259,781.

(Continued)

(51) Int. Cl.
*A61B 8/00* (2006.01)
*A61B 8/06* (2006.01)
(Continued)

(52) U.S. Cl.
CPC ............... *A61B 8/481* (2013.01); *A61B 8/06* (2013.01); *A61B 8/0816* (2013.01);
(Continued)

(58) Field of Classification Search
CPC ......... A61B 8/481; A61B 8/06; A61B 8/0816; A61B 8/0891; A61N 7/00; A61N 2007/0039
See application file for complete search history.

(56) References Cited

U.S. PATENT DOCUMENTS 6,443,896 B1   9/2002   Detmer
6,530,885 B1   3/2003   Entrekin et al.
(Continued)

FOREIGN PATENT DOCUMENTS

EP   0770352 A1   5/1997
EP   1790384 A1   5/2007
(Continued)

OTHER PUBLICATIONS

PCT/IB2017/057825 ISR and Written Opinion, dated Mar. 22, 2018, 15 Pages.

*Primary Examiner* — Joel Lamprecht

(57) ABSTRACT

A therapeutic ultrasound method configured to adaptively transmit ultrasound pulses toward microbubbles in a treatment region to remove an occlusion is described. In some examples, the system may include a treatment pulse unit configured to transmit an ultrasound pulse to a treatment region of a subject, the treatment region including a plurality of microbubbles. An echo detection unit may be configured to receive one or more echoes responsive to the ultrasound pulse. In some examples, the method may also include a data processor configured to identify, using data associated with the echoes, at least one echo signature indicative of a dynamic state of the microbubbles in response to the ultrasound pulse. A controller may be configured to adjust one or more parameters of an additional ultrasound pulse transmitted to the treatment region via the treatment pulse unit based on the at least one echo signature.

10 Claims, 8 Drawing Sheets

Related U.S. Application Data

(60) Provisional application No. 62/435,139, filed on Dec. 16, 2016.

(51) Int. Cl.
 *A61B 8/08* (2006.01)
 *A61N 7/00* (2006.01)

(52) U.S. Cl.
 CPC .............. *A61B 8/0891* (2013.01); *A61N 7/00* (2013.01); *A61N 2007/0039* (2013.01)

(56) References Cited

U.S. PATENT DOCUMENTS

| | | | |
|---|---|---|---|
| 11,259,781 B2 * | 3/2022 | Shi | ............................ A61B 8/06 |
| 2008/0125657 A1 | 5/2008 | Chomas et al. | |
| 2010/0160779 A1 | 6/2010 | Browning et al. | |
| 2014/0316329 A1 | 10/2014 | Soltani et al. | |

FOREIGN PATENT DOCUMENTS

| | | |
|---|---|---|
| WO | 2008039449 A1 | 4/2008 |
| WO | 2012042423 A1 | 4/2012 |
| WO | 2015000953 A1 | 1/2015 |
| WO | 2016092414 A1 | 6/2016 |

\* cited by examiner

ADAPTIVE PULSING FOR SONOTHROMBOLYSIS TREATMENT

RELATED APPLICATION

This application is a continuation of U.S. patent application Ser. No. 16/469,764 filed on Jun. 14, 2019, which in turn is the U.S. National Phase application under 35 U.S.C. § 371 of International Application No. PCT/IB2017/057825, filed on Dec. 12, 2017, which claims the benefit of and priority to U.S. Provisional Application No. 62/435,139, filed Dec. 16, 2016. These references are incorporated herein in their entirety.

BACKGROUND

Emerging treatments for ischemic stroke may include sonothrombolysis. Generally, sonothrombolysis may involve the use of focused ultrasound pulses to insonify microbubbles, an ultrasound contrast agent, flowing through a patient's vascular system in the vicinity of the occlusion, such as a clot, responsible for the stroke. In particular, ultrasound pulses may often be delivered through the skull temporal bone of a patient, targeting microbubbles congregating at the clot site. Energy received from the ultrasound pulses may cause mechanical oscillation of the microbubbles at the site of the clot, which may contribute to ischemic stroke treatment by dissolving the clot over time, thus recanalizing the occluded vessel(s) and re-initiating blood flow therethrough. An advantage of sonothrombolysis treatments incorporating only ultrasound pulses and microbubble oscillation is that they may be performed non-invasively and without the use of drugs, which are limited by significant use restrictions, potential adverse events, and overall low treatment success.

SUMMARY

The present invention relates to an improved approach for ultrasound pulsation during sonothrombolysis treatments, in which the ultrasound dose applied to the treatment region, microbubble preservation, and reduction in temporal bone heating is optimized. The present invention comes from a recognition that the heat generated by the ultrasound transducer during such sonothrombolysis treatments often limits its feasibility and effectiveness. For instance, to minimize heating at the transducer/skull interface while adequately sonifying a target volume for clot lysis, the focus of the ultrasound beam needs to be swept across the targeted clot site and surrounding tissue, as the target volume is typically larger than the transducer's focal zone and the entire target volume needs to be exposed to ultrasound for effective sonothrombolysis treatment. Additionally, ultrasonic pulsation may cause excessive destruction of the microbubbles at the clot site or even before the microbubbles can reach the clot site.

To avoid excessive heating, minimize microbubble destruction, and otherwise improve sonothrombolysis approaches, ultrasound systems and methods for adaptively pulsing microbubbles present within a treatment region of a subject are provided herein. In various examples, ultrasound pulses may be transmitted via a transducer to a treatment region containing an intravascular occlusion, such as a clot. Ultrasound echoes reflected from the microbubbles present within this region may then be received by a transducer, which may be the same or different than the transducer used for pulse transmittal. Echo signatures identified by processing the received echoes may reveal information about the microbubbles and/or the occlusion present at the treatment region. For example, echo signatures may be indicative of various dynamic states of the microbubbles induced by ultrasonic energy delivered via the pulses. Information regarding microbubble concentration and distribution, as well as the level of microbubble decay, may also gathered via the echo signatures. In response to the identified echo signatures, one or more parameters of an additional ultrasound pulse may be adjusted, and the additional pulse transmitted into the treatment region. In some examples, the parameters may include pulse length, frequency, and/or intensity, one or more of which may be modified to avoid destroying microbubbles away from the site of the occlusion and/or maximize microbubble excitation at the occlusion. The process of transmitting pulses, receiving echoes, processing the echo data, adjusting pulse parameters, and transmitting modified pulses may be repeated as necessary to effectively remove an occlusion present within the treatment region. By adapting the pulses in response to data regarding the effectiveness of a previously transmitted pulse to excite microbubbles and/or remove an occlusion, the systems provided herein may avoid excessive microbubble excitation, which may cause microbubble destruction, and selectively deliver ultrasound energy to particular locations only as necessary, thus minimizing the heat generated during successive pulsations.

In accordance with some examples, a therapeutic ultrasound system may include a treatment pulse unit configured to transmit an ultrasound pulse to a treatment region of a subject, the treatment region including a plurality of microbubbles. The therapeutic ultrasound system may further include an echo detection unit, which may be configured to receive one or more echoes responsive to the ultrasound pulse. The therapeutic ultrasound system may also include a data processor in communication with the echo detection unit. The data processor may be configured to identify, using data associated with the echoes, at least one echo signature indicative of a dynamic state of the microbubbles in response to the ultrasound pulse. The therapeutic ultrasound system may further include a controller in communication with the data processor. The controller may be configured to adjust one or more parameters of an additional ultrasound pulse transmitted to the treatment region via the treatment pulse unit based on at least one echo signature. In some examples, at least one echo signature may be indicative of microbubble concentration, microbubble distribution, a level of microbubble decay, and/or a level of microbubble oscillation within the treatment region or one or more sub regions thereof.

In some examples, the treatment pulse unit may be further configured to transmit two or more series of ultrasound pulses into the treatment region. In embodiments, the controller may be further configured to adjust one or more parameters of the ultrasound pulses transmitted in each series based on one or more echoes received by the echo detection unit in response to a preceding series of ultrasound pulses. In some examples, the treatment pulse unit may be further configured to transmit a first series of ultrasound pulses, each pulse in the first series having an equal length and intensity. In various embodiments, one or more parameters may include pulse intensity, pulse length, and/or pulse transmission direction. In some examples, the treatment region may include at least one intravascular occlusion. In embodiments, the treatment pulse unit may be further configured to transmit ultrasound pulses having one or more different parameters to different sub-regions. The data processor may be further configured to estimate a therapeutic effect of one or more ultrasound pulses based on at least one echo signature. In embodiments, the data processor may be further configured to determine an average echo intensity value generated by the microbubbles in the treatment region after transmitting a series of ultrasound pulses thereto. In some examples, the data processor may be further configured to compare the average echo intensity value to one or more echo intensities determined by the data processor. In various implementations, the controller may be further configured to match a duration of one or more ultrasound pulses to a duration of one or more echo signatures, where the echo signatures are derived from a sub-region into which the pulses are transmitted. In some examples, the therapeutic ultrasound system may further include a user interface configured to receive one or more user inputs, where the controller is further configured to adjust one or more parameters of the ultrasound pulses in response to the user inputs.

A method in accordance with the present disclosure may include transmitting an ultrasound pulse to a treatment region of a subject, the treatment region comprising a plurality of microbubbles. The method may further involve receiving one or more echoes responsive to the ultrasound pulse. The method may also involve identifying, using data associated with the echoes, at least one echo signature indicative of a dynamic state of the microbubbles in response to the ultrasound pulse, and adjusting one or more parameters of an additional ultrasound pulse transmitted to the treatment region based on at least one echo signature. In some examples, the echo signature may be indicative of microbubble concentration, microbubble distribution, a level of microbubble decay, and/or a level of microbubble oscillation within the treatment region or one or more sub-regions thereof.

In some examples, the treatment region may include at least one intravascular occlusion and the ultrasound pulses may be configured to cause the microbubbles to oscillate at a level sufficient to remove the occlusion. In embodiments, the method may further involve comparing echo signatures to threshold echo intensity values. In some implementations, transmitting ultrasound pulses to a treatment region may involve transmitting a focused ultrasound beam having a focal zone to the treatment region and steering the ultrasound beam to move the focal zone across the treatment region. In various embodiments, an ultrasound intensity of the focal zone may be automatically adjusted while moving the focal zone across the treatment region. In embodiments, the steps of transmitting, receiving, identifying, and adjusting may be repeated until the microbubbles cause an occlusion positioned within the treatment region to be removed therefrom. Some examples may further involve ultrasonically imaging the treatment region.

Additionally, any of the techniques for adaptively pulsing microbubbles to remove an occlusion may be embodied in executable instructions, which when executed may cause one or more processors of an ultrasound system to be programmed to perform the processes embodied in the non-transitory computer-readable medium.

DETAILED DESCRIPTION

Figure 1:
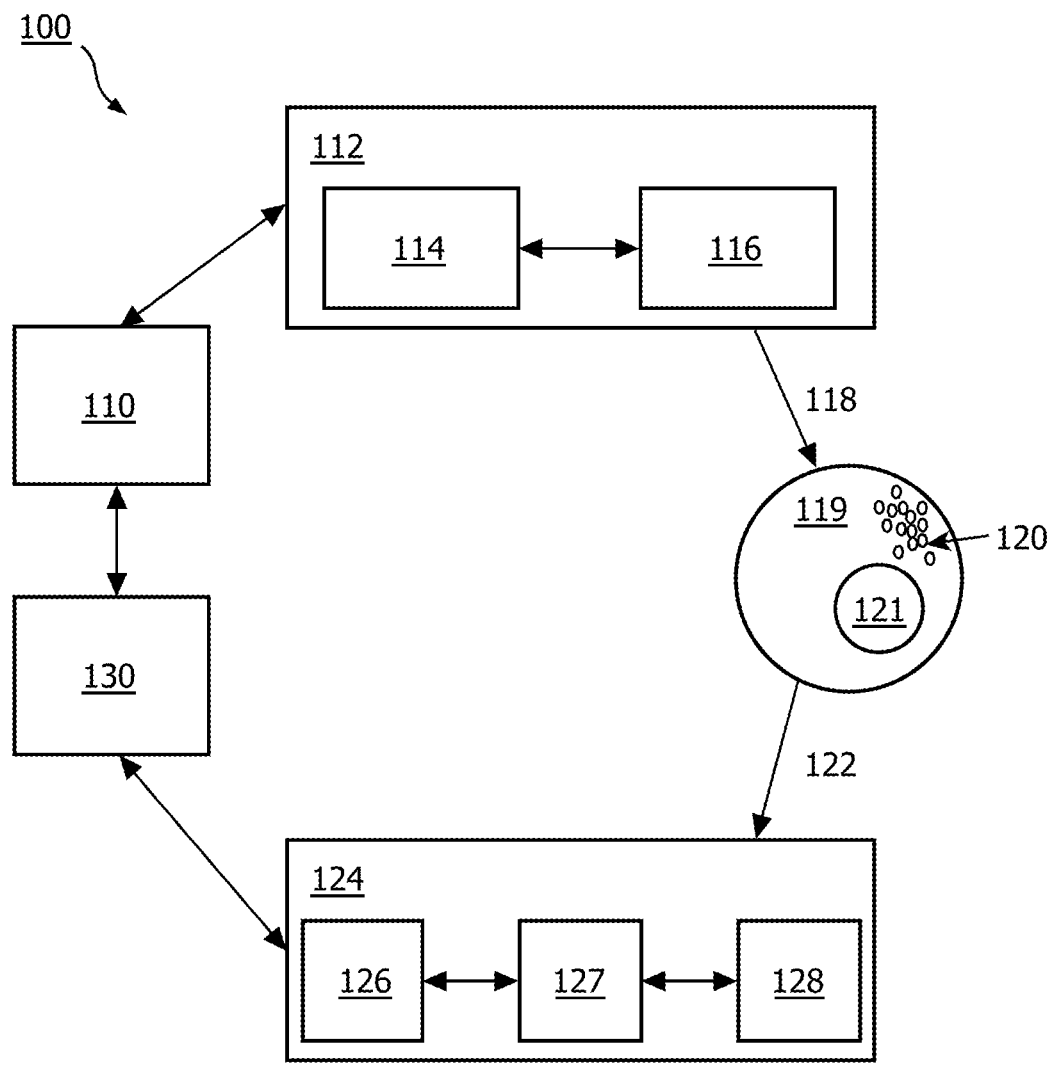
FIG. 1 is a block diagram of a therapeutic ultrasound system in accordance with the principles of the present disclosure.

The following description of certain exemplary embodiments is merely exemplary in nature and is in no way intended to limit the invention or its applications or uses. For example, embodiments are described in the context of sonothrombolysis techniques, however, the systems, methods and apparatuses described herein may be applied to any transcranial procedure that involves electronically steering an ultrasound array across a treatment region to expose microbubbles flowing therein. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

The present technology is also described below with reference to block diagrams and/or flowchart illustrations of methods, apparatus (systems) and/or computer program products according to the present embodiments. It is understood that blocks of the block diagrams and/or flowchart illustrations, and combinations of blocks in the block diagrams and/or flowchart illustrations, may be implemented by computer program instructions. These computer program instructions may be provided to a processor, controller or controlling unit of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

Sonothrombolysis treatment of an occlusion in the vascular system may typically involve sonifying a population of injected and/or infused microbubbles at the occlusion site with a series of focused ultrasonic pulses. The pulses may be transmitted over multiple rounds or series of ultrasonic exposure, each round including a plurality of pulses. The presence of microbubbles at the site of the occlusion during each ultrasound exposure, and the effective excitation of these microbubbles, may be crucial for effective sonothrombolysis treatment. Because microbubble impact and survival may depend on the length and/or intensity of each ultrasonic pulse transmitted into the treatment region, the pulse parameters may require close monitoring and control. For example, long therapeutic pulses or pulse sequences may cause excessive microbubble destruction or otherwise prevent effective mechanical action of the microbubble oscillations, herein referred to as microbubble "cavitation."

The systems and methods described herein may optimize sonothrombolysis treatment by adaptively adjusting the parameters of ultrasound pulses in response to microbubble echo data, e.g., echo signatures or sets, received from various locations within a treatment region. The disclosed methods may account for differences in the local arrival time and/or concentration of microbubbles at various locations within the treatment region, particularly between the occlusion center and surrounding or downstream ischemic region, by emitting ultrasound pulsing sequences that adapt to local contrast flow. Utilizing microbubble echo data to adjust pulse intensity, duration, and/or direction during each successive round of ultrasound exposure in the multi-round treatment regime described herein may maximize or increase the concentration of microbubbles that reach the clot site of an occluded vessel by avoiding unnecessary off-target microbubble activation. Relatedly, the effectiveness of microbubble cavitation at the occlusion site may also be increased. Furthermore, the adaptive pulsing techniques disclosed herein may minimize or decrease the total ultrasound energy transmitted via the skull bone and into the brain, thus reducing the amount of heat generated during treatment.

FIG. 1 shows an example therapeutic ultrasound system 100 configured to optimize microbubble concentration and/or cavitation at an occlusion site during sonothrombolysis treatment. As shown, the system 100 may include a controller 110 which is coupled to a therapeutic pulse unit 112. In the example shown, the therapeutic pulse unit 112 includes at least a treatment transducer 114 operable to transmit pulses of ultrasound and a treatment beamformer 116. The therapeutic pulse unit 112 may be configured to transmit one or more pulses 118 into a treatment region 119. As shown, the treatment region 119 may include a population of microbubbles 120. The treatment region 119 may also define one or more sub-regions 121, the dimensions and location of which may be determined by the system 100 and/or based on user input. Ultrasound energy delivered by the pulses 118 may be absorbed and/or reflected by the microbubbles 120, thereby generating one or more microbubble echoes 122 which may be received by an echo detection unit 124. The echo detection unit 124 includes, in the embodiment shown, at least an imaging transducer 126, an imaging beamformer 127, and a signal processor 128 collectively configured to detect the echoes 122 generated responsive to the transmitted pulses 118 to the treatment region 119. As further shown, the echo detection unit 124 may be coupled to a data processor 130. In embodiments, the data processor 130 may be configured to identify, using data associated with the echoes 122, one or more echo signatures indicative of a dynamic state of the microbubbles in response to an ultrasound pulse 118. In some examples, various echo signatures may be indicative of microbubble concentration, microbubble distribution, levels of microbubble decay, and/or levels of microbubble oscillation/cavitation based on the ultrasound data, e.g., echo data, received and/or processed by the echo detection unit 124. The data processor 130 may be configured to communicate this information to the controller 110, which may be configured to adjust one or more parameters of the pulses 118 transmitted from the therapeutic pulse unit 112 in a subsequent treatment round based on the echo signatures. In some embodiments, the functions of the treatment transducer 114 and imaging transducer 126 may be performed by a single transducer, and similarly, the functions of the treatment beamformer 116 and imaging beamformer 127 may be performed by a single beamformer of the ultrasound system 100. In embodiments, the system 100 can be a stand-alone therapeutic ultrasound system either fixedly mounted or equipped with wheels to enable movement. The system 100 can be a compatible, portable device such as a laptop, a tablet, a smart phone or the like in some examples. The treatment transducer 114 and/or imaging transducer 126 can be connectable, for example via a USB interface, to any suitable portable device.

In an example operation, the controller 110 may be configured to instruct the therapeutic pulse unit 112 to generate and transmit a first series of pulses 118 into the treatment region 119. Microbubbles 120 present within the treatment region 119 may oscillate and emit ultrasonic echoes 122 responsive to the pulses 118, which are then received and/or processed by the echo detection unit 124. Ultrasound data associated with the echoes 122 (also referred to herein as "echo data") may be transmitted from the echo detection unit 124 to the data processor 130 for additional processing. Using the information gleaned from the echoes 122 by the echo detection unit 124 and the data processor 130, the controller 110 may be configured to adjust one or more parameters of the pulses 118 transmitted into the treatment region 119 via the therapeutic pulse unit 112 in a second series of pulses 118.

The treatment region 119 may be selectable by one or more users, e.g., physicians, clinicians, sonographers, ultrasound technicians, or combinations thereof. According to embodiments of the present disclosure, the treatment region 119 may encompass at least a portion of a blood vessel which may be located in the brain. The blood vessel may contain an occlusion, e.g., a clot or intravascular build-up. In some examples, the clot or build-up may have previously caused the patient to experience a stroke. In other examples, treatment effected by the system 100 may be preventive in nature, initiated in response to the detection of one or more build-ups or clots within the vascular system but not yet causing complete blood flow blockage. In some embodiments, the system 100 may target blood vessels in the vicinity of cerebral tissue exhibiting pathologic qualities, such as cancerous growth patterns, neurodegenerative biochemistry, and/or any malady that may benefit from delivering one or more drugs across the blood-brain barrier.

In various embodiments, the treatment region 119 may include one or more sub-regions 121. The number of sub-regions 121, and the dimensions thereof, may vary in different implementations. For example, each sub-region 121 may be sized equally or differently than other sub-regions 121 within the treatment region 119. For example, a treatment region 119 encompassing nine cubic centimeters may be divided into three sub-regions 121, each sub-region defined by a volume of three cubic centimeters. During operation of the system 100, each sub-region 121 may be targeted by a single pulse 118. In some examples, the sub-regions 121 may be defined by the echoes 122 detected during one or more rounds of ultrasound treatment. For instance, a first treatment round may reveal a number of distinct microbubble echoes 122 or sets of echoes, the echoes associated with a specific time point during the ultrasound exposure of the first round. Based on the time point that the echoes 122 are received by the echo detection unit 124, the system 100 may determine which localized area within the treatment region 119 coincides with which echoes 122. In this manner, the time points may be used to link received echoes 122 to one or more sub-regions 121.

The number and composition of the microbubbles 120 flowing within the treatment region 119 may vary in different embodiments. Generally, the microbubbles 120 may include contrast microbubbles configured to improve and/or enable acoustic monitoring of an occlusion site. Microbubbles 120 may include, for example, any gas or liquid encapsulated within a lipid, protein, or polymer coating. Various concentrations of microbubbles 120 may be administered intravenously to a patient from various points of entry. The microbubbles 120 may be administered in fluid mixture, solution, or suspension. After a certain period of time, a patient's vascular system may carry the population of injected microbubbles 120, or at least a portion thereof, into the treatment region 119, where they may be targeted by the therapeutic pulse unit 112. Microbubble cavitation at the treatment region 119 may depend on the length, frequency content, and/or intensity of the pulses 118 directed at the microbubbles 120. In some examples, the state of microbubble cavitation may reflect the effectiveness of one or more pulses 118 for treating an occlusion.

To transmit pulses 118 toward the microbubbles 120 present within the treatment region 119 and any sub-regions 121, the therapeutic pulse unit 112 may include an ultrasonic treatment transducer 114. The treatment transducer 114 may be a component held and manipulated by a user during operation of the system 100. The treatment transducer 114 may be configured to transmit ultrasonic energy into the treatment region 119 in the form of one or more pulses 118, e.g., beams, which may be transmitted in series. In operation, the treatment transducer 114 may be scanned across the volume of the treatment region 119, transmitting a series of pulses 118 during the scan. In embodiments, the treatment transducer 114 may be configured to adjust one or more parameters of each individual pulse 118 such that pulses 118 emitted at different time points during the scan to different sub-regions 121 may have different properties, e.g., length and/or intensity. A variety of treatment transducers 114 are well known in the art, e.g., linear arrays, convex arrays or phased arrays. In some examples, the treatment transducer 114 may be a three-beam transducer configured to simultaneously transmit pulses 118 in the form of three separate ultrasound beams into the treatment region 119. In embodiments, the number of pulses 118 emitted from the treatment transducer 114 in any given series of pulses may vary.

As further shown in FIG. 1, the treatment transducer 114 may be coupled to a treatment beamformer 116, e.g., a microbeamformer. The treatment beamformer 116 may be configured to direct the transmission of pulses 118 such that the beamformed pulses 118 are steered straight ahead from (orthogonal to) the treatment transducer 114, or at different angles. By adjusting the direction that each pulse 118 is emitted, pulses having various lengths and/or intensities may be directed toward different sub-regions 121. The treatment beamformer 116, alone or in combination with the treatment transducer 114, may be configured to align discrete ultrasonic beams concurrently emitted from the transducer such that the beams converge at a focal zone within the treatment region 119. During a scan, the focal zone may be swept across the treatment region 119. The depth and/or dimensions of the focal zone may vary, and may depend on the number, size, and/or location of one or more targeted occlusions within the treatment region 119.

As further shown in FIG. 1, the system 100 may include a controller 110 operatively, physically, and/or communicatively coupled to the therapeutic pulse unit 112. The controller 110, e.g., computational module or circuitry, may be configured to dictate one or more parameters of each pulse 118 by providing commands to the therapeutic pulse unit 112, such as to control operation of the beamformer. The sonothrombolysis pulse treatments disclosed herein may be executable in discrete, sequential rounds of ultrasound exposure at the treatment region 119, each round including a series of pulses 118. Before each round, the controller 110 may be configured to adjust the parameters of one or more pulses 118 based on data received at the echo detection unit 124 and processed by the data processor 130, such that each successive treatment round may be responsive to the echo data generated in the preceding treatment round, the data indicative of dynamic microbubble echo signatures, microbubble concentration, and/or the nature of microbubble cavitation in different sub-regions 121, for example. In this manner, the system 100 may be configured as an adjustable feedback loop.

In operation, the pulses 118 emitted by the therapeutic pulse unit 112 under the direction of the controller 110 may be sufficient to cause microbubbles 120 present within the treatment region 119 to oscillate, thereby causing various levels of microbubble cavitation. Depending on the location and intensity of microbubble cavitation, the cavitation may clear an occluded blood vessel. The pulses 118 may also cause the destruction of at least a portion of the microbubbles 120. Thus, removing the occlusion may occur gradually over multiple rounds of ultrasonic pulsation. The characteristics of each pulse 118, as well as the number of pulses emitted in each round, may vary. For example, the length, frequency, and/or direction of each pulse 118 may be modified. One or more parameters of each pulse 118 may be adjusted to induce microbubble cavitation without causing excessive microbubble destruction.

For example, the therapeutic pulse unit 112 may transmit a plurality of pulses 118 into the treatment region 119 at a constant or variable frequency. Pulse frequency may vary depending on the size and/or composition of the targeted occlusion, the number of anticipated treatment rounds, the duration of each pulse 118, and/or the data generated from previous treatment rounds. In embodiments, pulse frequency may be determined empirically, such that one or more pulse frequencies are selected based on the level of cavitation achieved with similar pulse frequencies. In some examples, the pulse frequency may range from about 0.5 MHz to about 3.0 MHz, about 0.8 MHz to about 2.5 MHz, about 1.2 MHz to about 2.2 MHz, or about 1.5 MHz to about 1.7 MHz.

The length of each pulse 118 may also vary. For instance, where a plurality of pulses 118 is transmitted, each pulse may have the same or different length. The length of one or more pulses 118 may also be determined empirically, based on the length of previously-emitted pulses 118 and the state of microbubble cavitation achieved as a result, for example. In some embodiments, the length of each pulse 118 may range from about 1 µs to about 1 second. In particular embodiments, the pulse length may range from about 1 µs to about 10 µs, about 5 µs to about 15 µs, about 10 µs to about 20 µs, about 15 µs to about 25 µs, about 20 µs to about 30 µs, about 25 µs to about 35 µs, about 30 µs to about 40 µs, about 35 μs to about 45 μs, about 40 μs to about 50 μs, about 45 μs to about 55 μs, about 50 μs to about 60 μs, about 55 μs to about 65 μs, about 60 μs to about 70 μs, about 65 μs to about 75 μs, about 70 μs to about 80 μs, about 75 μs to about 85 μs, about 80 μs to about 90 μs, about 85 μs to about 95 μs, about 90 μs to about 100 μs, about 100 μs to about 500 μs, about 500 μs to about 1 ms, about 1 ms to about 5 ms, about 5 ms to about 10 ms, about 10 ms to about 15 ms, about 15 ms to about 20 ms, or about 20 ms to about 25 ms. Additional embodiments may include pulse lengths greater than 25 ms, up to about 1 second, for example.

The direction each pulse 118 is transmitted into the treatment region 119 may also vary, and may be adjustable by the controller 110 in each treatment round. Because the therapeutic pulse unit 112 may be configured to scan across the treatment region 119 while transmitting pulses 118, pulses emitted at different times may be emitted in different directions. For example, a first pulse may be transmitted at a first angle at a first time point, a second pulse may be transmitted at a second angle, different from the first angle, at a second time point, different from the first time point, and so on. The therapeutic pulse unit 112 may be configured to transmit pulses 118 in multiple distinct directions, ranging from about 1 to about 50 directions in various embodiments. The scanning angle over which the different pulses 118 are transmitted may also vary, along with the degree of separation between each pulse 118. In some embodiments, the pulses 118 may be transmitted within a sector area between about 1° and about 180°, about 1° and about 60°, about 40° to about 60°, or about 50° to about 60°. Discrete pulses 118 may be distributed equally or unequally within the sector area of each scan.

Subjecting microbubbles 120 present within the treatment region 119 to the pulses 118 may cause the microbubbles 120 to oscillate and reflect ultrasonic echoes 122. As further shown in FIG. 1, the system 100 may include an echo detection unit 124 configured to receive such echoes 122. The echo detection unit 124 may include an imaging transducer 126, an imaging beamformer 127, and a signal processor 128. Together, the components of the echo detection unit 124 may be configured to continuously listen and monitor scattered and reflected echoes 122 originating from the microbubbles 120 as the pulses 118 are transmitted thereto. In some embodiments, such as when the same transducer and beamformer are used for both the pulses and imaging, the echo detection unit 124 may be configured to listen for echoes during the time intervals between transmission of the pulses.

In some examples, the imaging transducer 126 may be an acoustic passive cavitation detector or a cavitation imager. As such, the imaging transducer 126 may be a listening and/or imaging device which in some examples may not be configured to transmit ultrasonic energy into the treatment region 119, but rather to receive echoes 122 responsive to the pulses 118 emitted by the therapeutic pulse unit 112. The imaging transducer 126 may be a component held and manipulated by a user. The imaging beamformer 127 may be coupled within the imaging transducer 126, controlling the reception of echoes 122 by the transducer elements positioned therein. In particular, the imaging beamformer 127 may be configured to beamform scattered signals into coherent echoes 122.

The type of imaging executable by the imaging transducer 126 in different embodiments may vary. Examples in which the imaging transducer 126 is configured as a cavitation imager may provide additional spatial and/or temporal data illustrative of the concentration, distribution and/or flow of microbubbles 120, the progress of vessel recanalization, and/or the anatomical structures present at one or more locations within the treatment region 119. In some embodiments, the imaging transducer 126 may be configured to transmit imaging pulses, which may be distinct from the pulses 118 emitted from the therapeutic pulse unit 112. In some examples, one or more imaging pulses may be interleaved between consecutive pulses 118 within each treatment series. In other examples, the imaging pulses may be transmitted before and/or after each series. Imaging pulses transmitted by the imaging transducer 126 may generate imaging echoes distinct from the echoes 122 generated in response to the pulses 118. The imaging echoes may also be received and/or processed by the echo detection unit 124.

In some embodiments, the imaging transducer 126 may be configured to perform low-intensity contrast imaging, e.g., B-mode imaging. Low-intensity contrast imaging may enable the system 100 to observe vessel occlusions and/or vessel recanalization as successive rounds of pulses 118 are transmitted into the treatment region 119. Low-intensity contrast imaging may also enable verification of the presence of microbubbles 120 within one or more sub-regions 121 before and/or after transmitting one or more pulses 118 thereto. Low-intensity contrast pulses, e.g., B-mode pulses, may be shorter and/or lower in amplitude than the pulses 118 generated by the therapeutic pulse unit 112 to avoid interference with microbubble cavitation induced by the pulses 118, and/or additional microbubble destruction. For example, each imaging pulse may range from about 0.5 μs to about 10 μs, about 1 μs to about 5 μs, about 1 μs to about 3 μs, or about 1.5 μs to about 2.5 μs.

In addition or alternatively, the imaging transducer 126 may be configured to perform one or more additional types of imaging. For example, the imaging transducer 126 may be configured to perform Doppler flow imaging, e.g., color-Doppler flow imaging. According to such embodiments, the imaging transducer 126 may be configured to transmit Doppler pulses into the treatment region 119. The Doppler pulses may also be of short duration relative to the pulses 118, ranging in length from about 10 μs to about 20 μs in various embodiments. Doppler imaging may enable the system 100 to observe the velocity and/or direction that the microbubbles 120 are flowing through the treatment region 119. In additional embodiments, the imaging transducer 126 may be configured to perform bubble-type contrast imaging that may be distinct from B-mode imaging. Doppler flow imaging and/or bubble-type contrast imaging may be used to construct spatial maps within or near the treatment region illustrating vasculature and/or bubble concentration/distribution. Spatial maps created through these types of imaging may be combined, in some examples, with ultraharmonic and/or spectral energy maps.

In some examples, data associated with the echoes 122 received by the imaging transducer 126 may be communicated to the signal processor 128. The signal processor 128 may be configured to process the received echoes 122 in various ways, such as bandpass filtering, decimation, I and Q components separation, and harmonic signal separation. The signal processor 128 may be further configured to arrange the echo signals in the spatial relationship from which they were received to form at least one ultrasound data frame. Multiple ultrasound data frames received by the signal processor 128 may be arranged according to their order of receipt, forming a temporal sequence of frames.

The echo detection unit 124 may be configured to acquire, via the imaging transducer 126, imaging beamformer 127, and signal processor 128, ultrasound data corresponding to the treatment region 119 and/or sub-regions 121 thereof. Techniques utilized by a user to acquire such data, via the echo detection unit 124, may vary. In some examples, the imaging transducer 126 may be positioned on or near a patient's head. In particular embodiments, the imaging transducer 126 may be placed on a patient's contralateral temporal bone window, on the opposite side of the patient's head as the treatment transducer 114. In some examples, the placement of the imaging transducer 126 may be held in a stationary position against the patient's head during administration of the pulses 118.

FIG. 1 also shows the data processor 130 that may be communicatively coupled to one or all components of the echo detection unit 124. The data processor 130 and the echo detection unit 124 are shown in FIG. 1 as separate components, but in some embodiments, they may be implemented in a single unit. Whether integrated with the echo detection unit 124 or coupled thereto, the data processor 130 may be configured to receive and process ultrasound data, e.g., a plurality of ultrasound data frames, acquired by the echo detection unit 124. In particular, the data processor 130 may be configured to perform spectral analysis, alone or in combination with the echo detection unit 124, of the echoes 122 generated by microbubbles 120 present within the treatment region 119. In some embodiments, the data processor 130 may operate to process ultrasound data in real time.

While the signal processor 128 may process, e.g., filter, a portion of the ultrasound data, the data processor 130 may be specifically configured to identify and/or extract echo signatures associated with dynamic states, e.g., oscillations and destructions, of the microbubbles 120, and/or states of microbubble cavitation. Microbubble cavitation states recognized by the data processor 130 may include moderate oscillation, stable cavitation, and/or inertial cavitation. Echo signatures indicative of such states may show increased fundamental, sub- and/or ultraharmonics of the pulse excitation frequency, and/or broadband scattering. In particular, ultraharmonics of the excitation frequency may indicate stable cavitation of the microbubbles 120, while elevated noise bands and/or broadband scattering may indicate inertial cavitation. In addition, the intensity of the echoes 122 may generally correspond to the concentration of microbubbles 120, such that echo intensity data may be used to decipher microbubble location and/or distribution. In some examples, echo intensity may be proportional to microbubble concentration such that higher levels of echo intensity indicate greater microbubble concentrations. Changes in the echo signatures and/or measured echo intensities over time may also indicate various recanalization trends occurring within the treatment region 119. For example, a reduction in echo duration in a particular sub-region 121 over successive rounds of ultrasound exposure may indicate recanalization of an occlusion within the sub-region 121.

Using one or more identified echo signatures, the data processor 130 may be further configured to estimate the therapeutic effect of one or more pulses 118 within the treatment region 119 or various sub-regions 121. In some examples, therapeutic effectiveness may be determined automatically by the data processor 130 according to one or more algorithms executed by the processor. In others, one or more users operating the system 100 may determine whether one or more echo signatures 124 indicate effective or ineffective treatment. Additional implementations may involve a combination of user interpretation and automatic processing by the data processor 130 to determine therapeutic effectiveness. Such implementations may thus involve semi-automatic data processing. In some embodiments, the data processor 130 may be configured to compare ultrasound data associated with one or more echoes 122 to one or more threshold values, which may indicate a threshold of echo intensity, for example, required to achieve one or more microbubble cavitation states and/or cause an effective therapeutic effect. Threshold values may be derived empirically using one or more sets of sonothrombolysis and/or microbubble cavitation data.

In some implementations, the data processor 130 may be configured to determine an average echo intensity value, which the data processor 130 may designate as a reference point for comparison to newly-acquired, local echo intensities derived from one or more sub-regions 121. For example, during a single treatment round the data processor 130 may receive ultrasound data corresponding to a plurality of echoes 122. Collectively, the echoes 122 may span the entire treatment region 119, and echoes 122 may be more intense in certain sub-regions 121 harboring greater concentrations of microbubbles 120 than other sub-regions harboring fewer microbubbles, and vice-versa. The data processor 130 may be configured to average the echo intensities received across the treatment region 119, deriving an average echo intensity value. During subsequent treatment rounds, the data processor 130 may be configured to compare the average echo intensity value to the local echo intensity values for newly-acquired echo signatures, and use the results to guide the parameters of pulses 118 employed in the next treatment round. For instance, after determining that the intensity value of one or more echoes 122 is below the average echo intensity value, the data processor 130 may determine that the pulse parameters of one or more pulses 118 should be adjusted to direct more microbubbles to that particular sub-region. In another example, the data processor 130 may determine that a moderate to high echo intensity value detected in a particular sub-region aligns with a desired echo intensity value because, for example, that particular sub-region harbors the targeted occlusion. In such situations, the data processor 130 may determine that the intensity of one or more pulses 118 targeting that specific sub-region 121 should be reduced, or at least closely monitored, to avoid destroying the microbubbles 120 present at that location. Relatedly, the data processor 130 may determine that one or more sub-regions 121 not harboring an occlusion should not be subjected to pulses 118 having an above-average intensity level to avoid unnecessary microbubble oscillation and/or destruction.

In some examples, a time-series of echoes 122 may be analyzed by the data processor 130 to assess signal changes over time, thus revealing information regarding microbubble decay. This technique may thus provide one way of determining the length of time that one or more microbubbles 120 can remain in a given sub-region 121 during application of one or more pulses 118.

After analysis, the data processor 130 may be configured to communicate ultrasound data, e.g., echo signature data, to the controller 110, the data indicative of microbubble concentration, distribution, decay, and/or cavitation in different sub-regions 121. Based on this information, the controller 110 may be configured to automatically modify, e.g., according to one or more executable algorithms, one or more parameters of the pulses 118 generated and transmitted via the therapeutic pulse unit 112. In some embodiments, a user operating the system 100 may manually input pulse parameter adjustments into the controller 110 via a user interface, for example. Some embodiments may involve a combination of automatic adjustments and user-input adjustments, such that the controller 110 may operate to adjust treatment pulse parameters semi-automatically. The controller 110 may be configured to adjust one or more pulse parameters on an individual sub-region 121 basis, such that different pulse parameters may be modified by different amounts in different sub-regions, all within one round of pulsation treatment.

The correlation between the ultrasound data processed and/or produced by the data processor 130 and the adjustments implemented by the controller 110 may vary. In embodiments, the pulse parameter adjustments may be determined automatically using an algorithm executable by the data processor 130 and/or the controller 110 that relies on previously received echo information as input. In some examples, the length of one or more pulses 118 may be adjusted according to the length of the echoes 122 received at the receiving unit 124. For instance, in some embodiments the duration of a pulse 118 may be greater than the duration of the echoes 122 specifically responsive to the pulse. Data showing such a difference in signal duration may be indicative of microbubble decay or at least a low microbubble concentration in the particular sub-region 121 targeted by the pulse 118. In such situations, the controller 110 may be configured to decrease the duration of the next pulse 118 transmitted into the same sub-region 121 from the therapeutic pulse unit 112. For example, during the first treatment round, a pulse 118 transmitted into a particular sub-region 121 may last 20 milliseconds. If the echoes 122 responsive to the 20-millisecond pulse 118 last only 10 milliseconds, then the pulse 118 transmitted into the sub-region 121 during the second round may be shortened accordingly, for example, to 10 milliseconds. By contrast, the data processor 130 may determine that the duration of a given pulse 118 is equal to the duration of the echoes 122 specifically responsive to the pulse. In such a situation, the controller 110 may be configured to increase and/or maintain the duration of the next pulse 118 transmitted into the same sub-region 121. By reducing and/or matching the treatment pulse duration to the duration of the corresponding echo signature, the data processor 130 and/or controller 110 may reduce global microbubble destruction, thus preserving more microbubbles 120, and their cavitation activity, for the occlusion site. In some examples, reducing the length of one or more pulses 118 may also reduce the heat generated by the pulses.

The intensity, e.g., amplitude, of one or more pulses 118 may also be adjusted based on the data received and/or processed by the data processor 130. For example, in response to an echo signature indicative of microbubble destruction in a particular sub-region 121, the controller 110 may be configured to decrease the amplitude of the next pulse 118 transmitted into the same sub-region 121, thus avoiding or minimizing additional microbubble destruction in the sub-region 121. By contrast, the controller 110 may be configured to increase the intensity of one or more pulses 118 in response to echo data indicative of little to no cavitation occurring within a sub-region 121 that contains an occlusion. Like adjustments to pulse length, pulse intensity modifications may reduce microbubble destruction, especially in sub-regions where cavitation may be unnecessary, and reduce the amount of heat generated during operation of the system 100.

In some examples, the system 100 may also optimize the order by which particular sub-regions 121 undergo recanalization. For instance, in some examples initial recanalization of downstream microcirculation may allow the pulsatile blood pressure to be fully exerted on a primary occlusion within the treatment region 119, thereby increasing residual flow in a manner that may increase and/or optimize the speed and/or effectiveness of microbubble-induced recanalization.

Implementations of the adaptive pulsing executable by the system 100 may vary. For example, the therapeutic pulse unit 112 may transmit, in a first treatment round, a plurality of pulses 118 each having an average or maximal ultrasound dose, e.g., length and/or intensity. In some examples, the upper limits of the treatment pulse duration and/or intensity that define the maximal ultrasound dose used utilized during the first treatment round may be based on treatment-safe data. Reduced ultrasound doses having, for example, shorter durations and/or reduced intensity, may be determined by the data processor 130 and/or controller 110 based on the signatures identified in the echoes 122 received at the echo detection unit 124. The reduced ultrasound doses, which may vary between sub-regions 121, may be transmitted into the treatment region 119 in the form of a second round of pulses 118. As in the first treatment round, the ultrasound echoes 122 generated by the microbubbles 120 in response to the second round of pulses 118 may be detected by the echo detection unit 124 and processed by the data processor 130. The data processor 130, alone or in combination with the controller 110, may again modify the parameters of one or more pulses 118 in response to the length, intensity and/or cavitation signatures of the echoes 122 generated by the second round of pulses, thus guiding a third round of treatment. This process of adapting the parameters of one or more pulses 118 according to the magnitude and/or trend of echoes 122 derived from different sub-regions 121 may be repeated by the system 100 for any number of treatment rounds. For example, the number of treatment rounds may range from 1 to about 20 rounds, about 4 to about 16 rounds, about 8 to about 12 rounds, or about 9 to about 11 rounds. In various embodiments, adaptive pulsing schemes executable by the system 100 may be implemented via any suitable existing and future-developed algorithm.

Depending on the particular clinical application, CT-angiogram may also be used to obtain information regarding microbubble 120 concentration, location, and/or cavitation within the treatment region 119. In some examples, Mill may be used to obtain time-of-flight data indicative of the location of one or more blood vessels within the treatment region 119. These additional techniques may provide additional layers of data used collectively to determine location and concentration information regarding the microbubbles 120 at or near the treatment region 119.

Figure 2:
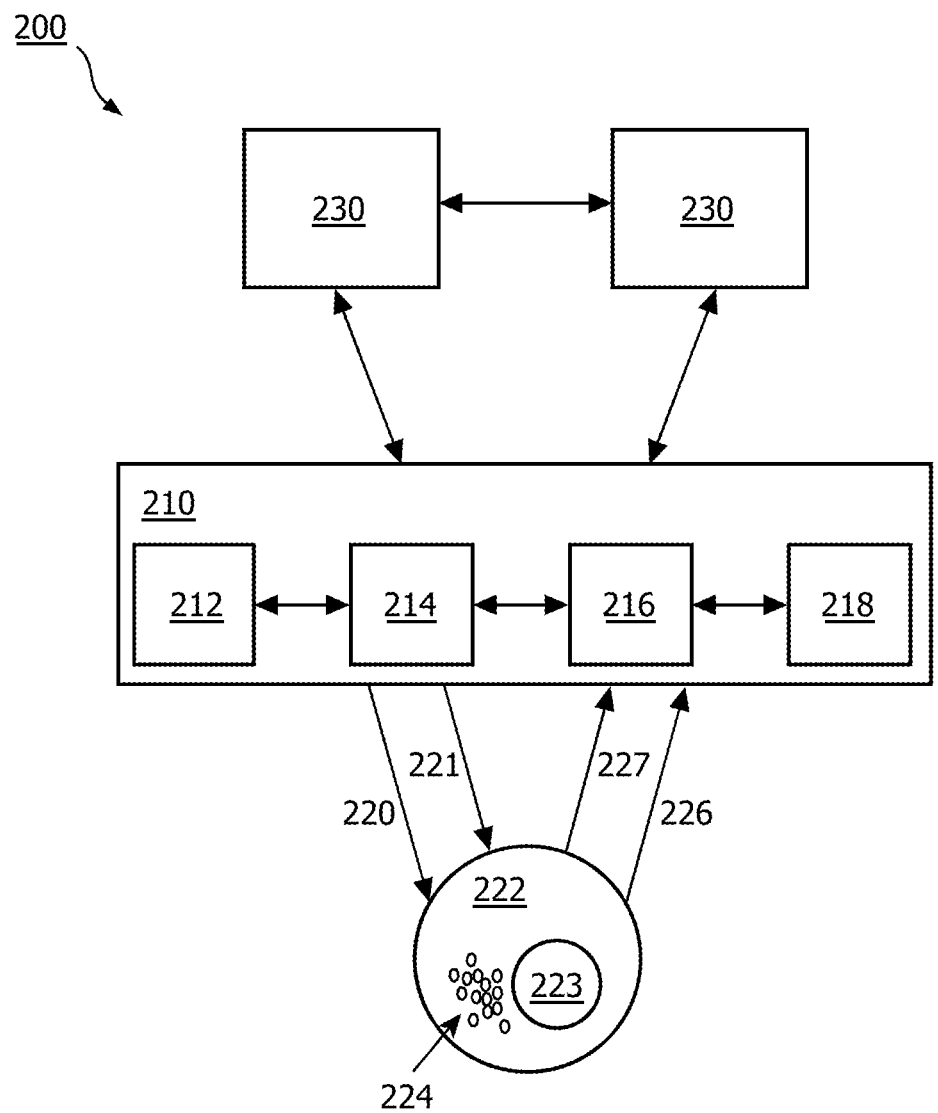
FIG. 2 is a block diagram of another therapeutic ultrasound system in accordance with the principles of the present disclosure.

FIG. 2 is a block diagram of another therapeutic ultrasound system in accordance with the principles of the present disclosure. The therapeutic ultrasound system 200 shown in FIG. 2 may include a single ultrasonic transceiver 210 configured to transmit pulses and receive corresponding echoes. Specifically, the transceiver 210 may include a treatment transducer component 212 and an echo receiver component 214. The transceiver 210 may further include a beamformer 216 and a signal processor 218. Together, the components of the transceiver 210 may be configured to generate and/or transmit one or more pulses 220 into a treatment region 222 and/or one or more sub-regions 223, which may harbor a population of intravascular microbubbles 224. Upon receipt of one or more pulses 220, the microbubbles 224 may emit one or more ultrasound echoes 226 responsive to the pulses. The echoes 226 may be received and/or processed by the transceiver 210. Data corresponding to the received echoes 226 may be transmitted to a data processor 228 communicatively coupled to the transceiver 210. As further shown, the data processor 228 may be coupled to a controller 230. The controller may be configured to adjust one or more parameters of the pulses 220 transmitted to the treatment region 222 via the transceiver 210 based one or more echo signatures identified by the data processor 228.

The system 200 illustrated in FIG. 2 may operate in a similar manner as the system 100 depicted in FIG. 1, such that the only operational differences may reflect the integration of a pulse transmitter component and microbubble echo receiver component into one, unitary transceiver 210. In some examples, the transceiver 210 may include two different channels: one pulse transmission channel and one echo detection channel. In some implementations, the transceiver 210 may be configured to operate the channels concurrently such that pulses 220 may be emitted from the transceiver 210 while echoes 226 are being detected. In other embodiments, the transceiver 210 may be configured to switch rapidly and/or automatically between a pulse transmission mode and an echo detection mode. According to such embodiments, the transceiver 210 may include separate transmission and detection channels, or a single channel configured to both transmit pulses 220 and receive echoes 226 responsive to the pulses. In various embodiments, the controller 230 may be configured to control the manner of mode switching and/or simultaneous transmission and detection executed by the transceiver 210.

In some embodiments, the transceiver 210 may also be configured to transmit one or more imaging pulses 221 and receive corresponding imaging echoes 227 responsive to the pulses 221. In such embodiments, the transceiver 210 may include one or more imaging channels. For instance, the transceiver 210 may include two additional channels: one for transmitting imaging pulses 221 and one for receiving imaging echoes 227 responsive to the pulses. In another example, the transceiver 210 may include only one additional channel, the channel configured to both transmit imaging pulses 221 and receive the corresponding echoes 227. In still other embodiments, the transceiver 210 may not include additional channels for transmitting imaging pulses 221 and/or receiving the corresponding echoes 227, such that the transceiver 210 may be further configured to transmit imaging pulses 221 from a treatment transducer component 212 and receive imaging echoes 227 via the echo receiver component 214. According to such embodiments, the treatment transducer component 212 may be configured to switch rapidly and/or automatically between the transmission of pulses 220 and imaging pulses 221.

As further shown in FIG. 2, the transceiver 210 may include a beamformer 216, e.g., a microbeamformer. The beamformer 216 may be configured to control both the transmission of pulses 220 and/or imaging pulses 227, and the reception of ultrasound echoes 226 and/or imaging echoes 227. In particular embodiments, the beamformer 216 may be configured to beamform the echoes 226, 227 to produce coherent echoes, such as ultrasound raw radiofrequency data.

Figure 3:
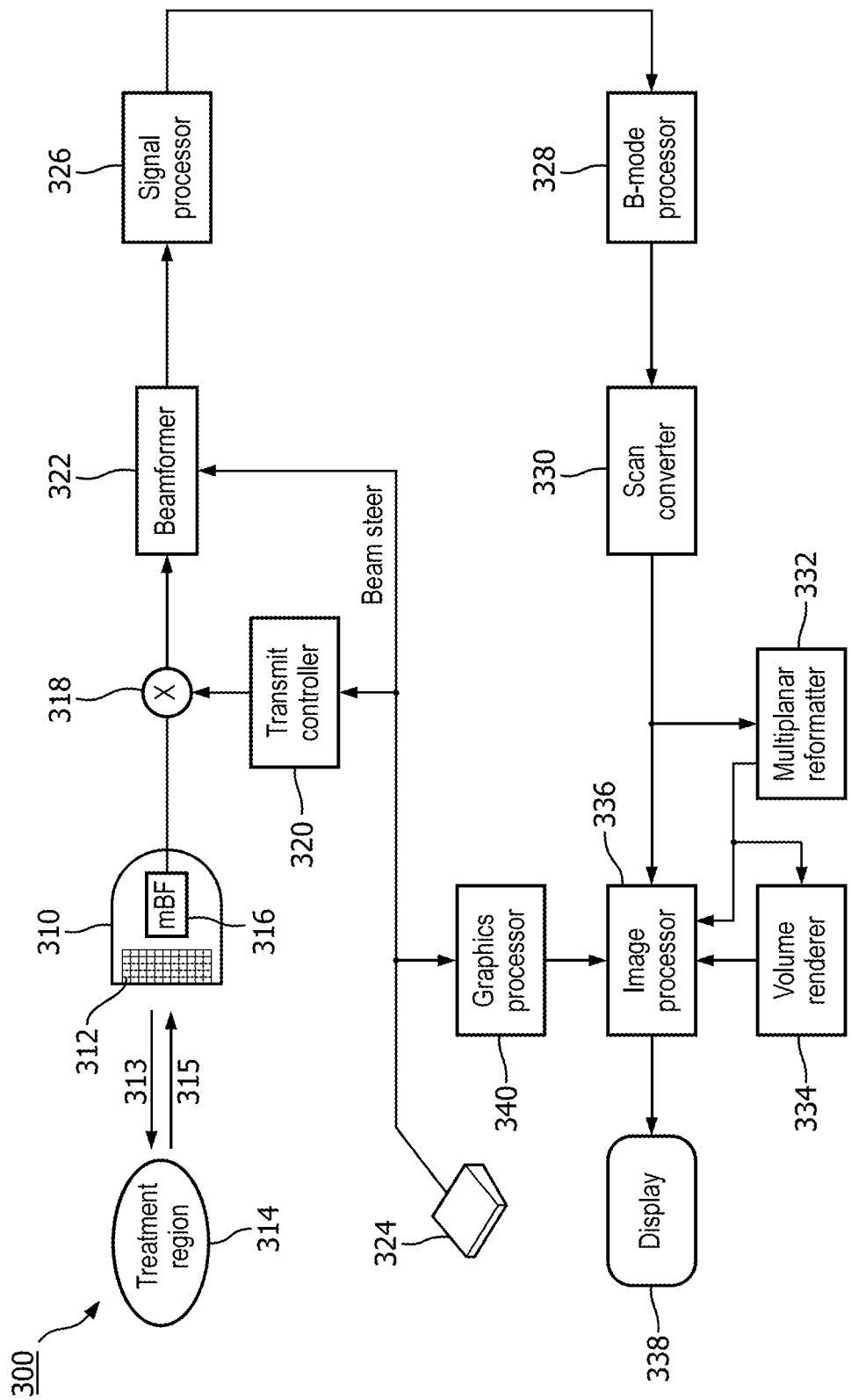
FIG. 3 is a block diagram of another therapeutic ultrasound system in accordance with principles of the present disclosure.

Referring to FIG. 3, a therapeutic ultrasound system 300 constructed in accordance with the principles of the present invention is shown in block diagram form. Like the system 200 shown in FIG. 2, the therapeutic ultrasound system 300 of FIG. 3 includes a single ultrasound transceiver 310. FIG. 3 also illustrates additional components, not shown in FIG. 1 or 2, which may be included within a system configured to adaptively pulse a treatment region containing microbubbles. For example, any of the above-described functions of the data processor 130 and/or 228 may be programmed (e.g., via computer executable instructions) into an existing processor of the system 300. In some embodiments, the functions of the data processor 130, for example, may be implemented in and/or controlled by one or more of the processing components shown in FIG. 3, including the processor 428, scan converter 430, multiplanar reformatter 432, volume renderer 434, and/or image processor 436.

The ultrasound transceiver 310 shown in FIG. 3 includes a transducer array 312 configured to transmit ultrasound beams or pulses 313 to a treatment region 314 and receive echo information 315. The transducer array 312 may include a two dimensional array (as shown) of transducer elements capable of scanning in both elevation and azimuth dimensions for 2D and/or 3D imaging. The transducer array 312 may be coupled to a microbeamformer 316 in the transceiver 310 which controls transmission and reception of signals by the transducer elements in the array. In this example, the microbeamformer is coupled by a transceiver cable to a transmit/receive (T/R) switch 318, which switches between transmission and reception and protects the main beamformer 322 from high energy transmit signals. In some embodiments, the T/R switch 318 and other elements in the system can be included in the transceiver 310 rather than in a separate ultrasound system base.

The transmission of ultrasonic beams or pulses 313 from the transducer array 312 under control of the microbeamformer 316 is directed by the transmit controller 320 coupled to the T/R switch 318 and the beamformer 322. As shown, the transmit controller 320 may be configured to receive input from the user's operation of a user interface or control panel 324. Based on the information displayed on the user interface and/or control panel 324, the user may adjust the ultrasound parameters of the beams 313 manually. In various embodiments, the transmit controller 320 may be configured to automatically adjust the ultrasound parameters, unless user input is received at the user interface 324, which may override one or more automatic functions executable by the transmit controller 320. Functions controlled by the transmit controller 320 may include the direction in which beams 313 are steered, as well as the length and/or intensity of the beams 313. The partially beamformed signals produced by the microbeamformer 316 may be coupled to a main beamformer 322 where partially beamformed signals from individual patches of transducer elements are combined into a fully beamformed signal.

As further shown in FIG. 3, the beamformed signals may be coupled to a signal processor 326. Like the signal processors 128, 218 shown in FIGS. 1 and 2, respectively, the signal processor 326 shown in FIG. 3 may be configured to process received echo signals 315 in various ways, such as bandpass filtering, decimation, I and Q component separation, and harmonic signal separation. The signal processor 326 may also perform additional signal enhancement such as speckle reduction, signal compounding, and noise elimination. The processed signals may be coupled to a processor 328, e.g., a B-mode processor, which may be configured to employ amplitude detection for the imaging of structures in the body, extract microbubble echo signatures, and/or compare echo information 315 received at the transceiver 310 to the parameters of the ultrasound beams 313. The signals produced by the processor 328 may be coupled to a scan converter 330 and a multiplanar reformatter 332. The scan converter 330 arranges the echo signals in the spatial relationship from which they were received in a desired image format. For instance, the scan converter 330 may arrange the echo signals into a two dimensional (2D) sector-shaped format, or a pyramidal three dimensional (3D) image. The multiplanar reformatter 332 can convert echoes which are received from points in a common plane in a volumetric region of the body into an ultrasonic image of that plane, as described in U.S. Pat. No. 6,443,896 (Detmer). A volume renderer 334 converts the echo signals of a 3D data set into a projected 3D image as viewed from a given reference point, e.g., as described in U.S. Pat. No. 6,530,885 (Entrekin et al.) The 2D or 3D images are coupled from the scan converter 330, multiplanar reformatter 332, and volume renderer 334 to an image processor 336 for further enhancement, buffering and temporary storage for display on an image display 338.

The graphics processor 336 may be configured to generate graphic overlays for display with the ultrasound images. These graphic overlays can contain, e.g., standard identifying information such as patient name, date and time of the image, imaging parameters, and the like. In some embodiments, the image display 338 may be configured to display acoustic ultrasound data and/or cavitation images. In some examples, the image display 338 may be configured to overlay microbubble cavitation data on anatomical structures imaged via B-mode imaging. For example, variations between the harmonic amplitude and/or signal duration detected between the beams 313 and the corresponding echo information 315 may be color-coded and mapped on an image of the treatment region 314, thus depicting spatial relationships between microbubble concentrations and/or microbubble cavitation in different areas within the treatment region 314. In response to the information displayed in the image display 338, a user may enter one or more inputs at the user interface 324. The user interface can also be coupled to the multiplanar reformatter 332 for selection and control of a display of multiple multiplanar reformatted (MPR) images.

Figure 4:
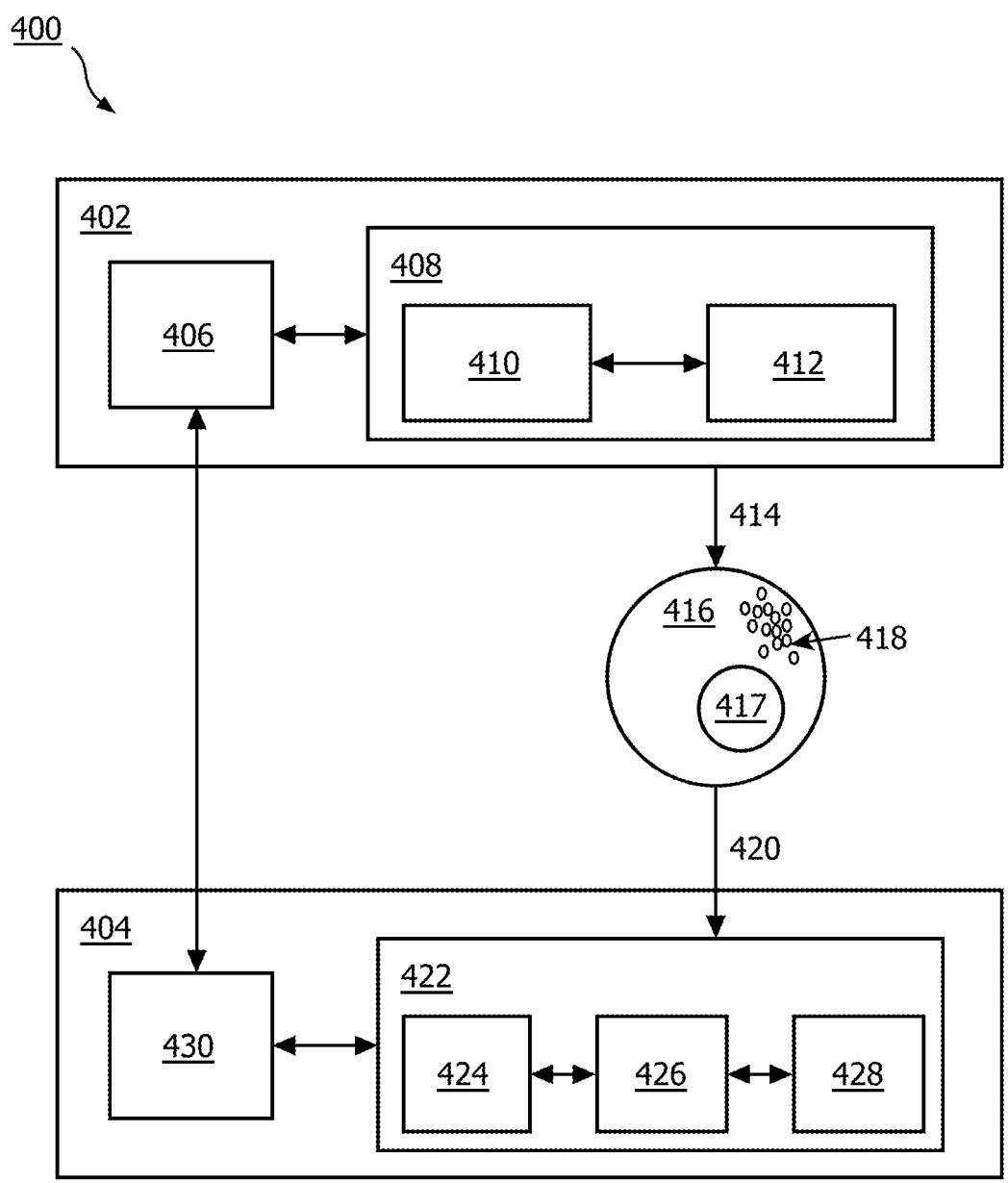
FIG. 4 is a block diagram of another therapeutic ultrasound system including two sub-systems in accordance with principles of the present disclosure.

FIG. 4 is a block diagram of another therapeutic ultrasound system in accordance with principles of the present disclosure. As shown, the therapeutic ultrasound system 400 may include a treatment sub-system 402 and a detection sub-system 404. The treatment sub-system 402 and the detection sub-system 404 may be communicatively coupled such that information and/or activity generated by one sub-system may be communicated to the other sub-system.

As further shown in FIG. 4, the treatment sub-system 402 may include a controller 406 coupled to a therapeutic pulse unit 408. The therapeutic pulse unit 408 may include a therapeutic treatment transducer 410 and a treatment beamformer 412. The therapeutic pulse unit 408 may be configured to generate and/or transmit one or more pulses 414 into a treatment region 416 and one or more sub-regions 417, which may include a population of microbubbles 418.

Ultrasound echoes 420 responsive to the pulses 414 may be received and/or processed by an echo detection unit 422 of the detection sub-system 404. In the embodiment shown, the echo detection unit 422 includes a receiving transducer 424, a receiving beamformer 426, and a signal processor 428. Ultrasound data corresponding to the echoes 420 may be communicated to a data processor 430 coupled to the echo detection unit 422, which may be configured to analyze the data to identify one or more echo signatures, echo durations, and/or echo intensity levels, for example. Ultrasound information generated by the data processor 430 may be communicated to the controller 406 of the treatment sub-system 402, which may then be configured to modify one or more parameters of a subsequent round of pulses 414 transmitted into the treatment region 416 by the therapeutic pulse unit 408.

The treatment sub-system 402 and the detection sub-system 404 may be defined by separate hardware, but in operation, may be configured to perform similarly to the components of the system 100 shown in FIG. 1. In particular, the treatment sub-system 402 may be configured to perform the same or similar tasks as the controller 110 and therapeutic pulse unit 112 shown in FIG. 1. Similarly, the echo detection sub-system 404 may be configured to perform the same or similar tasks as the echo detection unit 124 and data processor 130 shown in FIG. 1. As such, the echo detection sub-system 404 may be configured as a passive acoustic detector and/or a cavitation imager. In some embodiments, the echo detection sub-system may be configured to transmit imaging pulses, different from the pulses 414, into the treatment region 416, and receive the corresponding image echoes for additional processing.

In some examples, the sub-systems 402, 404 may be configured to operate in tandem by programming the hardware of one or both sub-systems accordingly. For example, such programming may cause the controller 406 to refrain from prompting the therapeutic pulse unit 408 to transmit one or more pulses 414 until data and/or commands are received by the data processor 430 of the echo detection sub-system 404.

Figure 5:
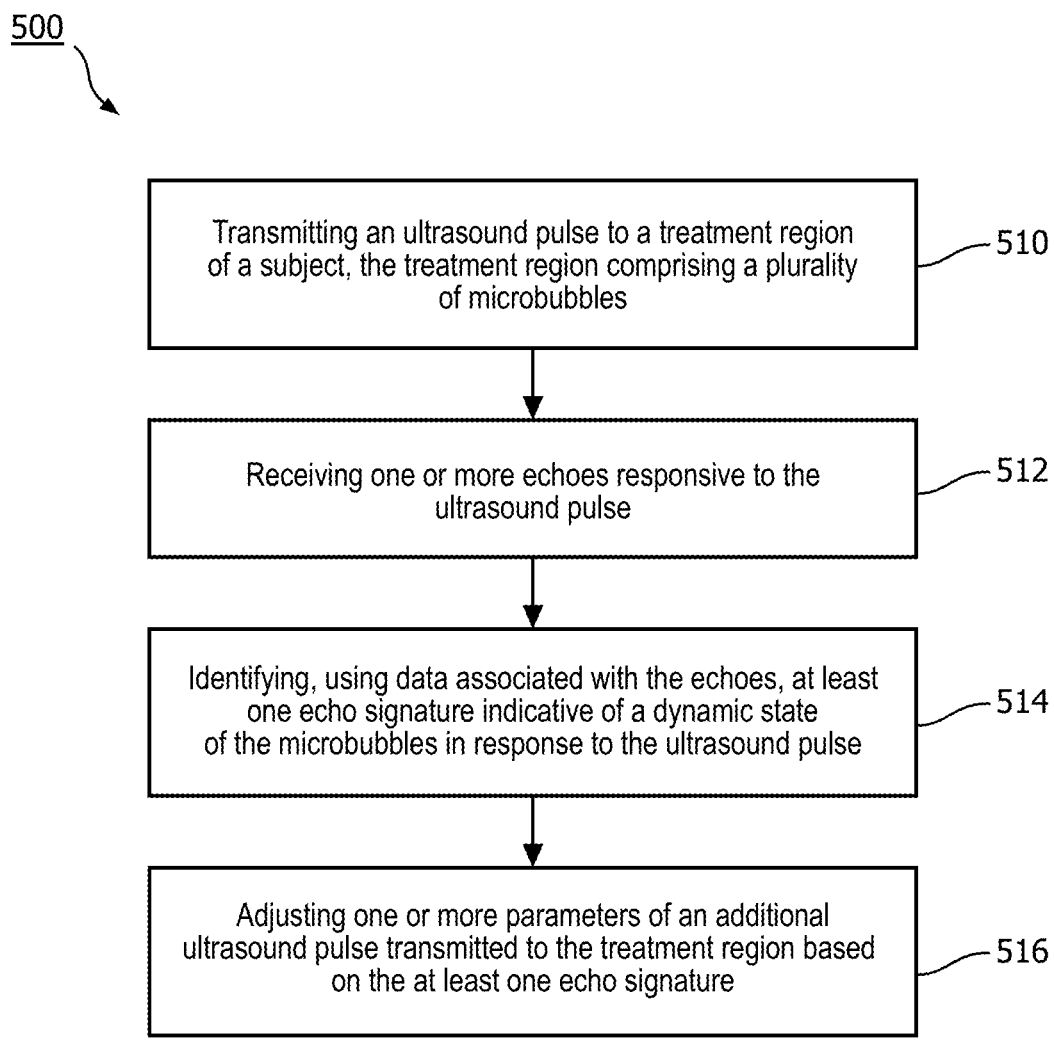
FIG. 5 is a block diagram of a therapeutic ultrasound method in accordance with the principles of the present disclosure.

FIG. 5 is a block diagram of a therapeutic ultrasound method in accordance with the principles of the present disclosure. The example method 500 of FIG. 5 shows the steps that may be utilized, in any sequence, by the systems and/or apparatuses described herein for optimizing sonothrombolysis treatment by adaptively adjusting the parameters of ultrasound pulses in response to microbubble echo data received from various locations within a treatment region. For instance, the method 500 may be performed by any of systems 100, 200, 300, and/or 400. The steps of the method 500 may be repeated until effective sonothrombolysis treatment is achieved.

In the embodiment shown, the method 500 begins at block 510 by "transmitting an ultrasound pulse to a treatment region of a subject, the treatment region comprising a plurality of microbubbles." In embodiments, the pulses may be transmitted to the treatment region using a treatment pulse unit which contains or is coupled to a treatment transducer. The treatment region may include at least a portion of a patient's brain that harbors at least one intravascular occlusion.

At block 512, the method involves "receiving one or more echoes responsive to the ultrasound pulse." In some examples, the echoes may be received by an echo detection unit, which may include one or more transducers. Additional embodiments may be configured to receive imaging echoes in response to imaging pulses also transmitted into the treatment region.

The method at block 514 involves "identifying, using data associated with the echoes, at least one echo signature indicative of a dynamic state of the microbubbles in response to the ultrasound pulse." In embodiments, the echo signature may be identified by a data processor in communication with an echo detection unit. The echo signature(s) may embody information regarding the duration and/or intensity of the echoes.

At block 516, the method involves "adjusting one or more parameters of an additional ultrasound pulse transmitted to the treatment region based on the at least one echo signature." In some examples, the parameters may be adjusted by a controller in communication with a data processor. Parameter adjustments may be made automatically, e.g., via an algorithm, and/or manually, e.g., via input from a user.

Adjusting one or more parameters may reduce microbubble destruction and/or may increase microbubble effectiveness by refraining from subjecting microbubbles present within a treatment region to excessively intense and/or long pulses.

It will be understood that each block of the flowchart, and combinations of blocks in the flowchart, may be implemented by various means, such as hardware, firmware, processor(s), circuitry and/or other devices associated with the execution of software including one or more computer program instructions. For example, one or more of the procedures described may be embodied by computer program instructions. In this regard, the computer program instructions which embody the procedures described above may be stored by a memory and executed by a processor. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block(s). These computer program instructions may also be stored in a computer-readable memory that may direct a computer or other programmable apparatus to function in a particular manner, such that the instructions stored in the computer-readable memory produce an article of manufacture which implements the functions specified in the flowchart block(s).

Figure 6:
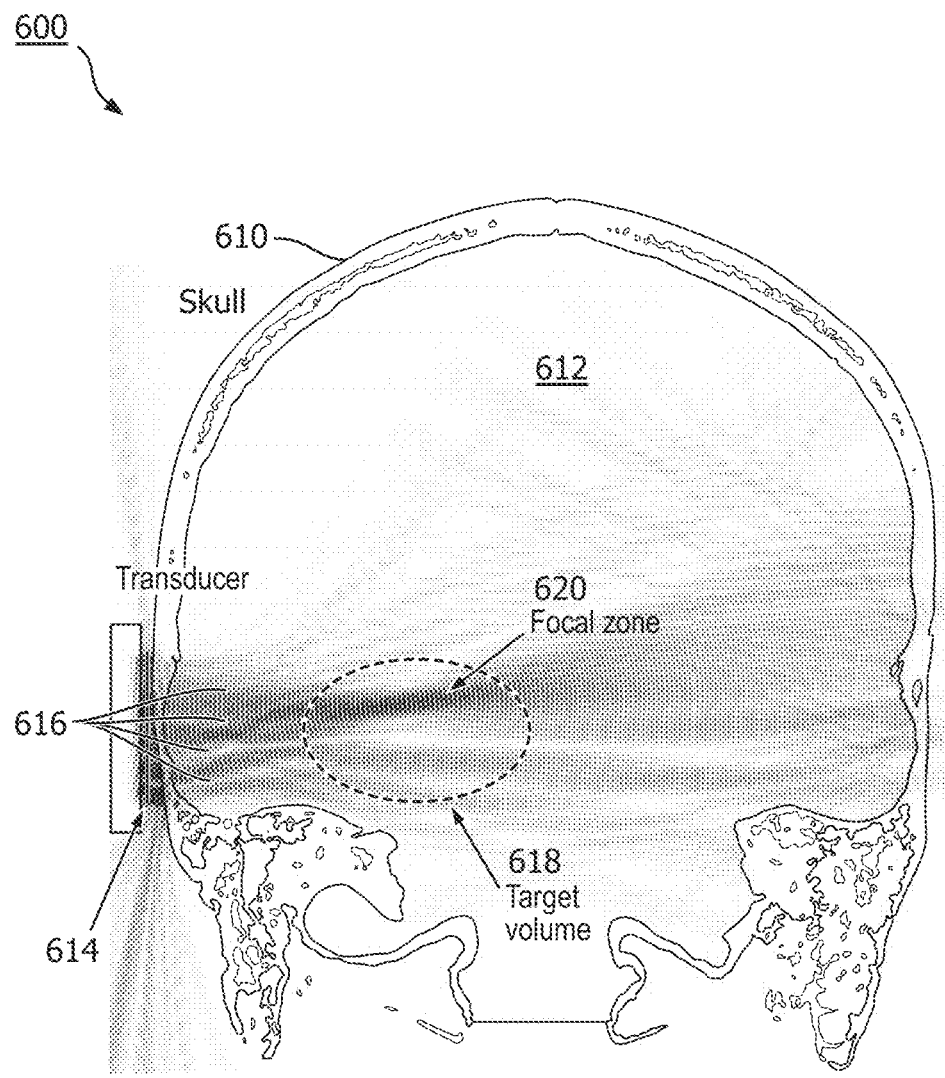
FIG. 6 is an image showing an arrangement of ultrasound beams being transmitted into a target volume within a patient's brain.

FIG. 6 is an image showing an arrangement of ultrasound beams being transmitted into a target volume within a patient's brain. FIG. 6 depicts a patient skull 610 surrounding a brain 612, and a transducer 614 transmitting a plurality of ultrasound beams 616 toward a treatment region or target volume 618. The ultrasound beams 616 converge at a focal zone 620 within the target volume 618.

As shown in FIG. 6, a plurality of ultrasound beams 616 may be directed toward the target volume 618. The beams 616 may embody pulses, such as the pulses 118 discussed above. Collectively, the beams 616 may be distributed across the target volume 618. At the focal zone 620, one or more beams 616 may converge to form a focused beam. In some examples, the depth of the focal zone 620 may be selected based on the depth and/or dimensions of the target volume 618. In embodiments, the location of the focal zone 620 may be adjusted according to one or more commands received from a controller communicatively coupled to the transducer 614.

Figure 7:
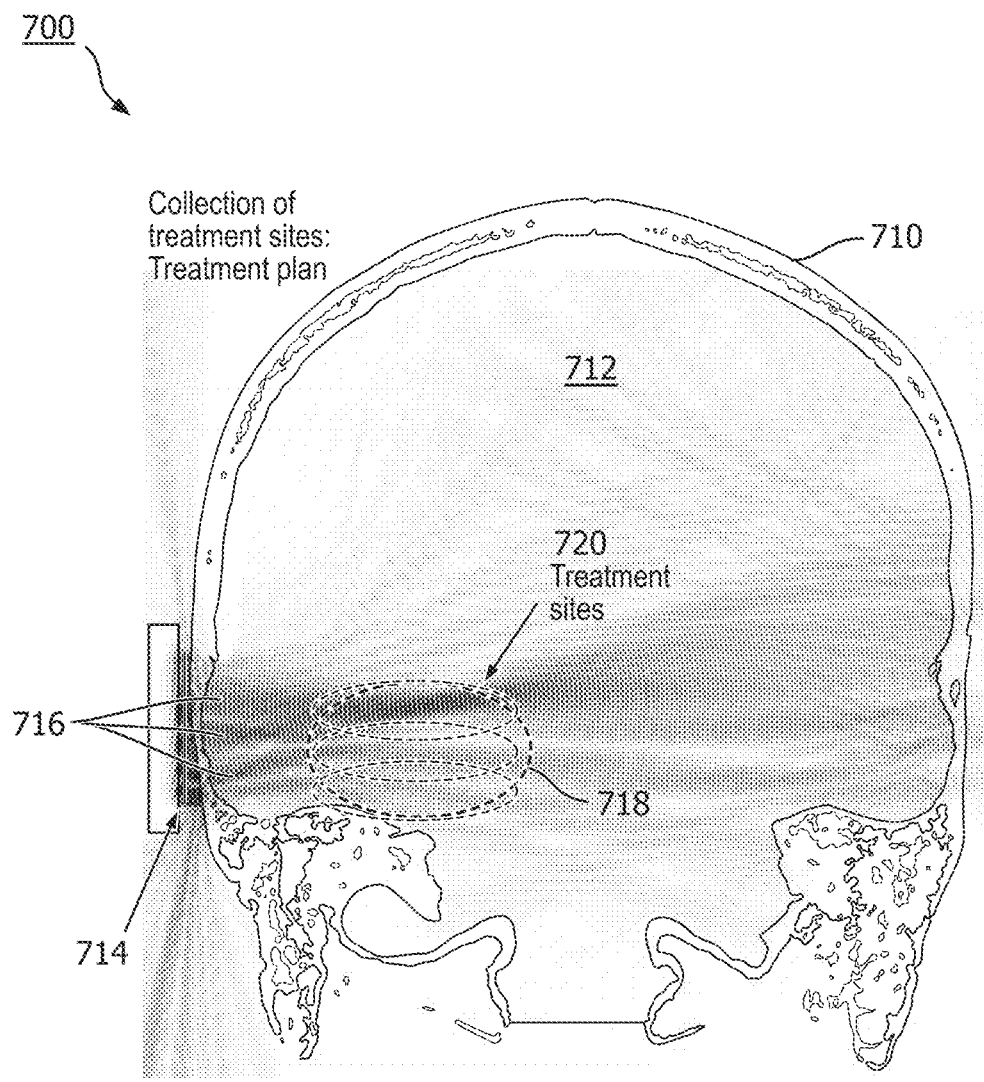
FIG. 7 is an image showing another arrangement of ultrasound beams being transmitted into the target volume illustrated in FIG. 6.

FIG. 7 is an image showing another arrangement of ultrasound beams being transmitted into the target volume illustrated in FIG. 6. Like FIG. 6, FIG. 7 illustrates a patient skull 710 surrounding a brain 712. A transducer 714 is shown transmitting a plurality of ultrasound beams 716 toward a treatment region or target volume 718. The beams 716 shown in FIG. 7 collectively target a plurality of treatment sites 720 within the target volume 718.

FIG. 7 illustrates that different ultrasound beams 716 may be used to target different or overlapping treatment sites 720. By adjusting the parameters of one or more ultrasound beams 716, different treatment sites 720 may be subjected to various levels of ultrasonic energy. For instance, one of the treatment sites 720 may be targeted by a beam 716 having a lower intensity than a beam 716 targeting another treatment site 720. In additional examples, the length of time that each beam 716 targets individual treatment sites 720 may also vary.

Figure 8:
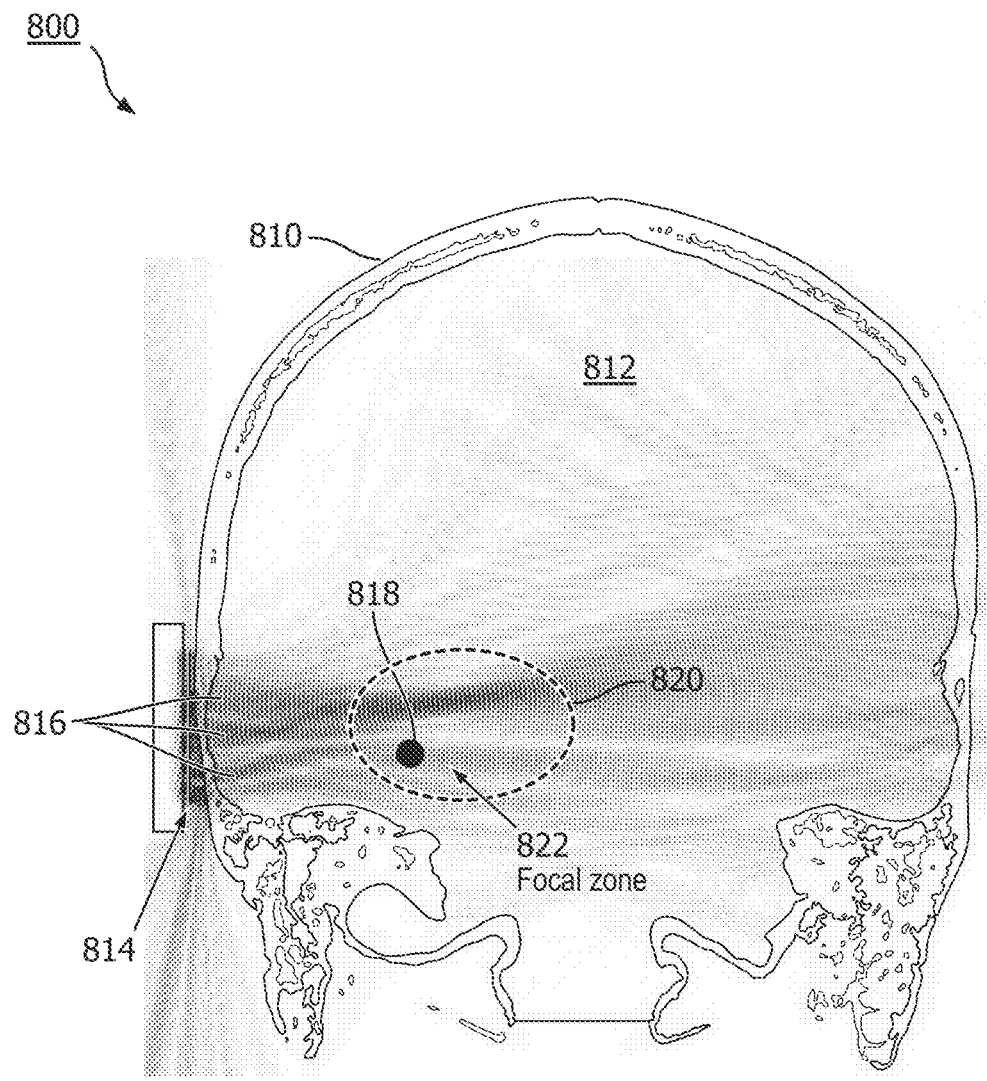
FIG. 8 is an image showing another arrangement of ultrasound beams being transmitted into the target volume illustrated in FIGS. 6 and 7.

FIG. 8 is an image showing another arrangement of ultrasound beams being transmitted into the target volume illustrated in FIGS. 6 and 7. FIG. 8 again shows a patient skull 810 surrounding a brain 812. As shown, a transducer 814 is transmitting a plurality of ultrasound beams 816 toward an occlusion 818 within the treatment region 820. At the site of the occlusion, the beams 816 are shown converging at a focal zone 822.

In embodiments, the focal zone 822 of the transducer 814 may be scanned or swept across the treatment region 820, targeting the occlusion 818 along the way. As the focal zone 822 is being swept across treatment region 820, the parameters of each ultrasound beam 816 may be adjusted, such that the collective strength of the focal zone 822 varies as it scans across the treatment region 820, subjecting different sub-regions to different levels of ultrasonic energy. For example, the transducer 814 may be configured to increase the intensity of the focal zone 822 and/or the length of time the focal zone 822 spends at the site of the occlusion 822, thereby increasing microbubble cavitation at that site. Likewise, the transducer 814 may be configured to decrease the ultrasound intensity at the focal zone 822 when the focal zone does not align with the occlusion 822 to minimize microbubble destruction in areas of the treatment region 820 not harboring the occlusion.

Of course, it is to be appreciated that any one of the examples, embodiments or processes described herein may be combined with one or more other examples, embodiments and/or processes or be separated and/or performed amongst separate devices or device portions in accordance with the present systems, devices and methods. The above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A method comprising:
    transmitting an ultrasound treatment pulse to a treatment region of a subject, the treatment region comprising a plurality of microbubbles;
    receiving one or more microbubble echoes comprising a reflection of the ultrasound treatment pulse by the plurality of microbubbles, wherein the received microbubble echoes is distinct from imaging echoes for ultrasonically imaging the treatment region;
    identifying, from the received microbubble echoes, at least one microbubble echo signature indicative of a dynamic state of the plurality of microbubbles in response to the ultrasound treatment pulse, wherein the at least one microbubble echo signature comprises at least one of:
        a frequency of the received microbubble echoes;
        an intensity of the received microbubble echoes; or
        a change over time of the intensity of the received microbubble echoes; and
    adjusting one or more parameters of an additional ultrasound pulse transmitted to the treatment region based on the at least one microbubble echo signature.

2. The method of claim 1, wherein the at least one echo microbubble signature is indicative of one or more of a microbubble concentration, a microbubble distribution, a level of microbubble decay, or a level of microbubble oscillation within the treatment region or one or more sub-regions thereof.

3. The method of claim 1,
wherein the treatment region comprises at least one intravascular occlusion, and
wherein the ultrasound treatment pulse is configured to cause the microbubbles to oscillate at a level sufficient to remove the at least one intravascular occlusion.

4. The method of claim 1, further comprising comparing the at least one microbubble echo signature to a threshold echo intensity value.

5. The method of claim 1, wherein transmitting the ultrasound treatment pulse to the treatment region comprises transmitting a focused ultrasound beam having a focal zone to the treatment region and steering the focused ultrasound beam to move the focal zone across the treatment region.

6. The method of claim 5, wherein an ultrasound intensity of the focal zone is automatically adjusted while moving the focal zone across the treatment region.

7. The method of claim 1, wherein the steps of transmitting, receiving, identifying, and adjusting are repeated until the at least one microbubble echo signature indicates that an occlusion positioned within the treatment region has been removed therefrom.

8. The method of claim 1, further comprising ultrasonically imaging the treatment region using the imaging echoes.

9. A non-transitory computer-readable medium comprising executable instructions, which when executed cause one or more processors of an ultrasound system to perform the method of claim 1.

10. An apparatus, comprising:
a controller configured to cause transmit of an ultrasound treatment pulse to a treatment region of a subject, the treatment region comprising a plurality of microbubbles; and
one or more processors configured to identify at least one microbubble echo signature indicative of a dynamic state of the plurality of microbubbles in response to the ultrasound treatment pulse,
wherein the at least one microbubble echo signature is identified from received microbubble echoes comprising a reflection of the ultrasound treatment pulse by the plurality of microbubbles,
wherein the received microbubble echoes is distinct from imaging echoes for ultrasonically imaging the treatment region,
wherein the at least one microbubble echo signature comprises at least one of:
a frequency of the received microbubble echoes;
an intensity of the received microbubble echoes; or
a change over time of the intensity of the received microbubble echoes, and
wherein the controller is configured to adjust one or more parameters of an additional ultrasound pulse transmitted to the treatment region based on the at least one microbubble echo signature.

\* \* \* \* \*